(12) United States Patent
Feld et al.

(10) Patent No.: US 7,986,141 B2
(45) Date of Patent: Jul. 26, 2011

(54) PATIENT BED WITH FORCE GENERATOR TO ASSIST OR EFFECT MOVEMENT OF A DEVICE PLUG IN A BED SOCKET

(75) Inventors: Peter Feld, Nürnberg (DE); Hubertus Fischer, Bamberg (DE); Wilfried Schnell, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 876 days.

(21) Appl. No.: 11/950,683

(22) Filed: Dec. 5, 2007

(65) Prior Publication Data

US 2008/0141461 A1 Jun. 19, 2008

(30) Foreign Application Priority Data

Dec. 5, 2006 (DE) .................. 10 2006 057 322

(51) Int. Cl.
*G01V 3/00* (2006.01)
(52) U.S. Cl. ............................ 324/318; 324/322
(58) Field of Classification Search .......... 324/300–322; 600/407–445
See application file for complete search history.

(56) References Cited

U.S. PATENT DOCUMENTS

| | | | | |
|---|---|---|---|---|
| 2,500,184 A | * | 3/1950 | Johnson et al. | 200/51.1 |
| 3,216,026 A | * | 11/1965 | Mann | 5/616 |
| 5,065,760 A | | 11/1991 | Krause et al. | |
| 5,749,374 A | * | 5/1998 | Schneider, Sr. | 128/870 |
| 6,229,310 B1 | * | 5/2001 | Green et al. | 324/318 |
| 6,254,410 B1 | | 7/2001 | Sugiyama et al. | |
| 6,943,552 B2 | * | 9/2005 | Renz | 324/318 |
| 7,602,182 B2 | * | 10/2009 | Heid et al. | 324/307 |
| 2007/0157385 A1 | * | 7/2007 | Lemire et al. | 5/600 |

FOREIGN PATENT DOCUMENTS

| | | |
|---|---|---|
| DE | 1 640 443 | 5/1970 |
| DE | 197 54 876 A1 | 6/1999 |

* cited by examiner

*Primary Examiner* — Brij B Shrivastav
(74) *Attorney, Agent, or Firm* — Schiff Hardin LLP

(57) ABSTRACT

A patient bed, in particular for a magnetic resonance apparatus, has at least one socket for accommodation of a plug of a device (in particular a local coil) to be arranged at the patient bed. A generation of a force generator that automatically assists or effects the insertion or the unplugging of the plug is built into the socket or is associated with the socket.

16 Claims, 5 Drawing Sheets

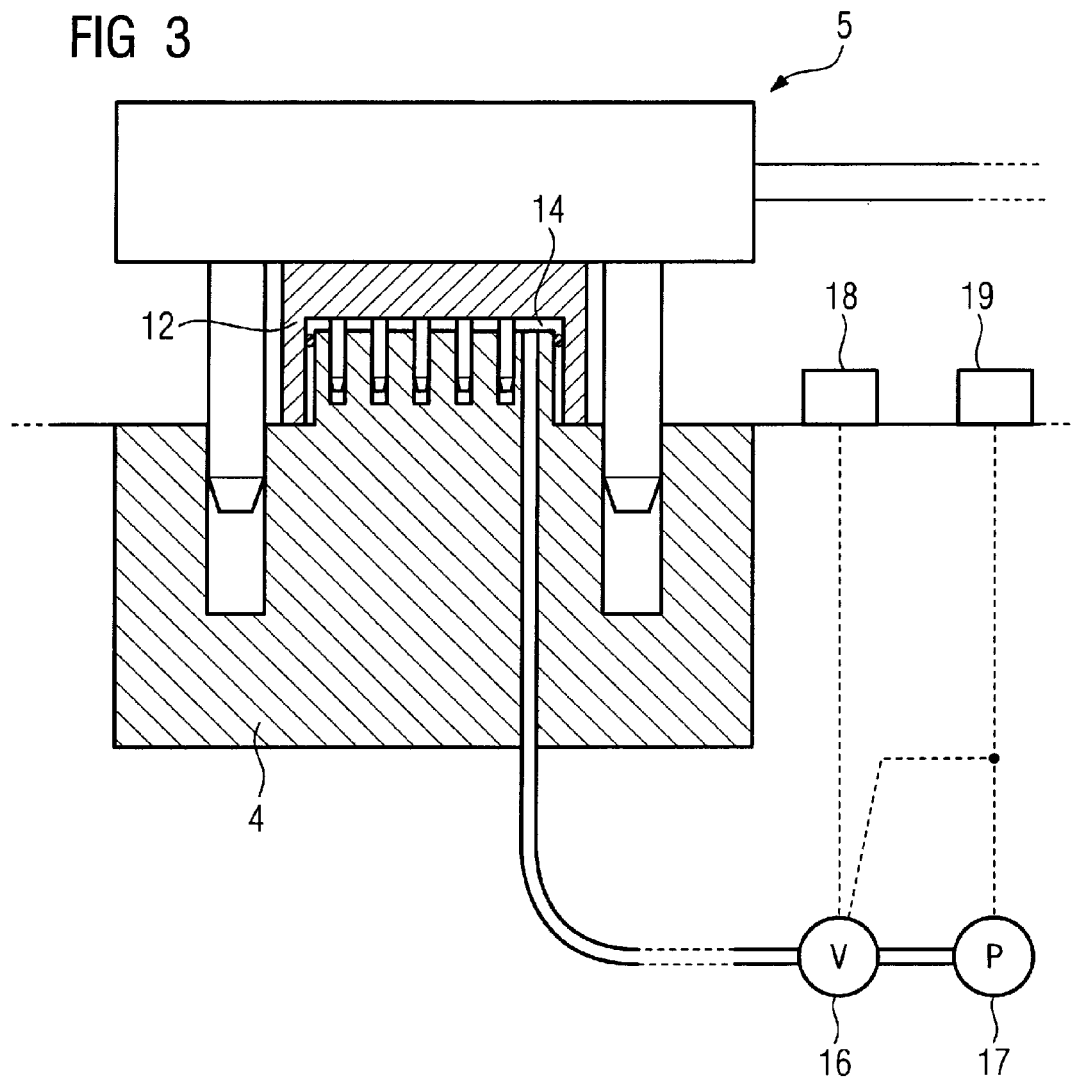

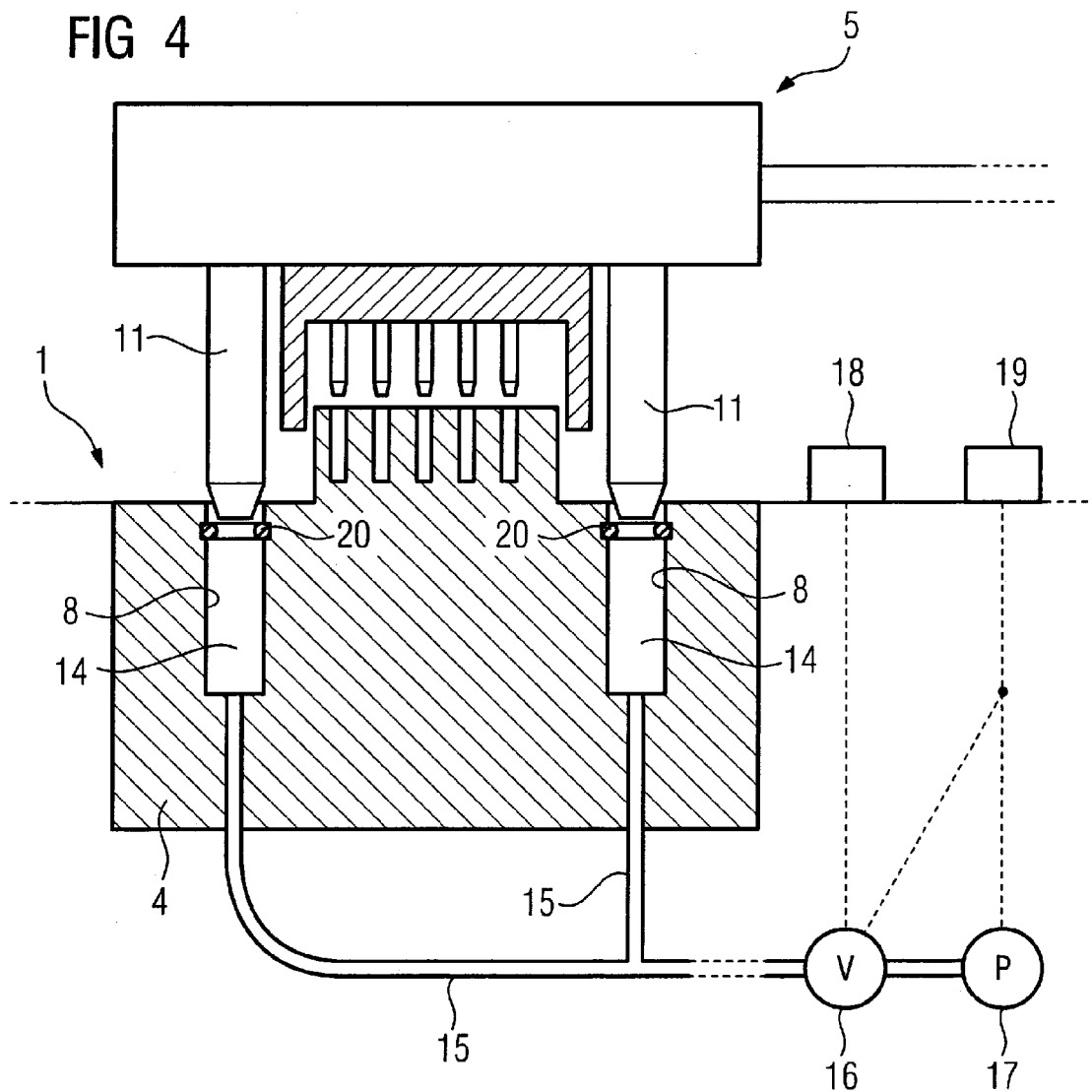

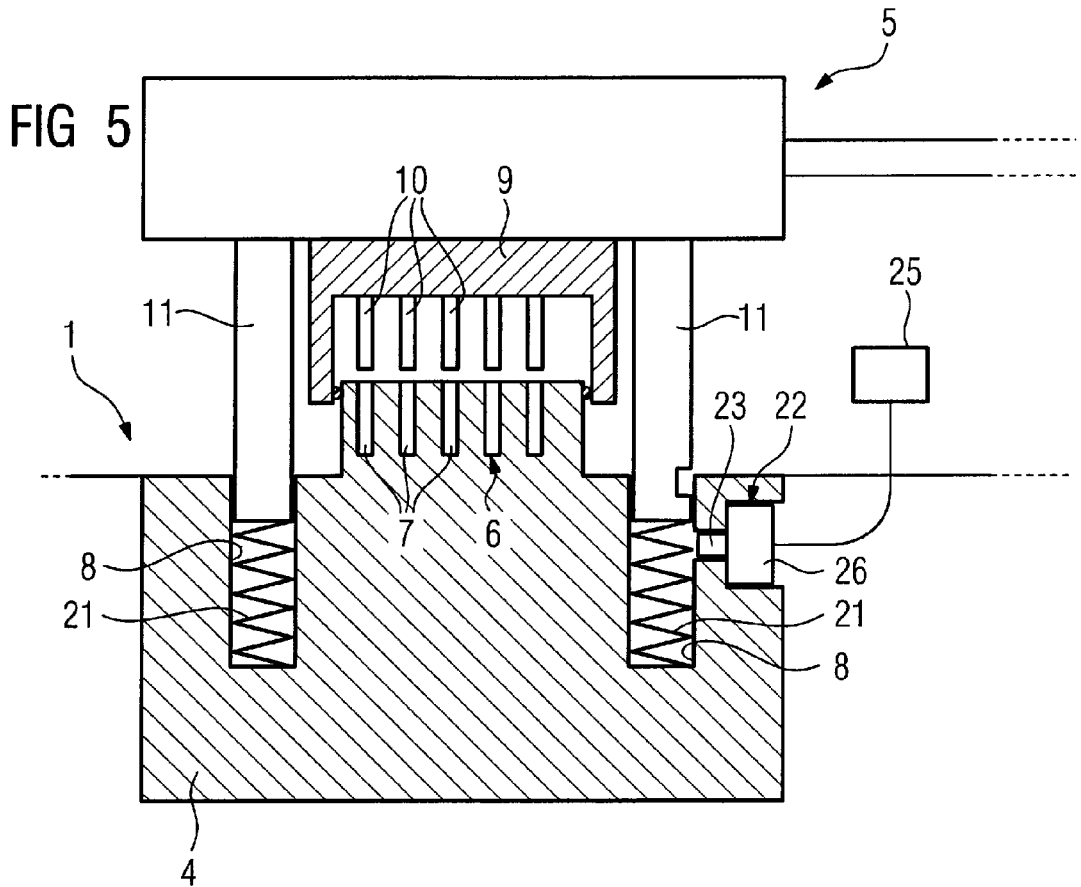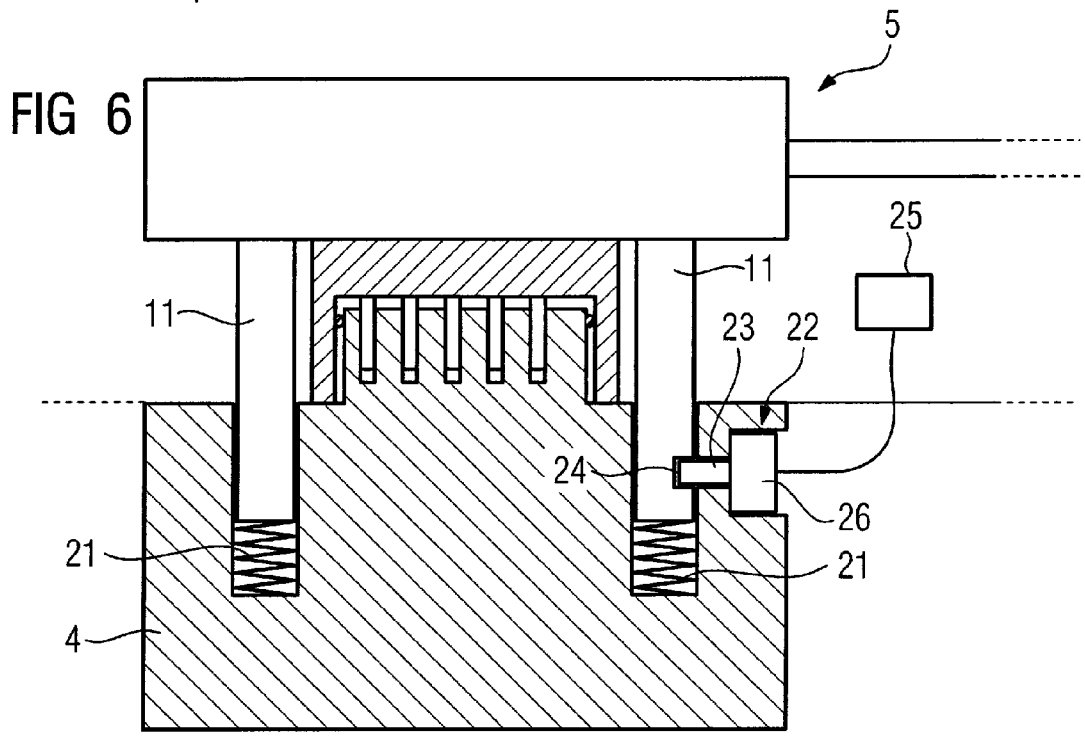

PATENT BEGINS

PATIENT BED WITH FORCE GENERATOR TO ASSIST OR EFFECT MOVEMENT OF A DEVICE PLUG IN A BED SOCKET

BACKGROUND OF THE INVENTION

1. Field of the Invention

The present invention concerns a patient bed, in particular for a magnetic resonance apparatus, of the type having at least one socket for accepting a plug of a device (in particular a local coil) to be arranged at the patient bed.

2. Description of the Prior Art

Primarily for patient beds used in magnetic resonance apparatuses, it is necessary to use special local coils for image acquisition of specific body regions. These local coils are typically arranged at the patient bed and are appropriately positioned relative to the patient. Signals originating from the examination or measurement volume are acquired by the local coil, and these signals are provided by signal conductors to the control and processing device of the magnetic resonance apparatus for image processing. For this purpose, a socket into which a plug is inserted is provided at the bed, and the coil signals are transferred to the conductor connections of the control and processing device conductor installed at the bed. After the end of the examination the local coil is removed again, by pulling the plug out of the socket.

A very good contacting between the plug and socket is typically required because very weak signals are normally acquired by the local coil, which is why in known plug-socket combinations the plug (which has a number of separate contacts) is very firmly accommodated in the socket contacts provided in identical number. While the plugging movement (in which the plug is, for example, placed vertically into the socket from above) is still relatively simple to effect by medical technology personnel, the unplugging is very labor-intensive and consequently difficult due to the very firm accommodation of the plug. The unplugging frequently is accomplished by jiggling somewhat at the plug or twisting the plug in order to loosen it, which can lead to deformation of the contacts if undertaken frequently. In order to simplify the unplugging it is known to provide a manually operated ejection aid that is located at a protective lid covering the socket, the protective lid being opened only when a plug is to be inserted. Two lever arms are provided at one end of the protective lid, these lever arms engaging below two lateral segments of the inserted plug in the opened position. For unplugging, the cover lid is further pivoted so that the lever arms strike the plug from below and push it out from the socket. It sometimes occurs that one or both arms break off due to the strong loading of the lever arms, or that the cover lid is over-pressured and is consequently ripped from its pivot bearing.

SUMMARY OF THE INVENTION

An object of the present invention is to provide a patient bed of the above type that is improved by exhibiting a safely functioning movement aid for moving the plug relative to the socket.

To solve this problem, in a patient bed of the aforementioned type, in accordance with the invention a force generator that automatically assists or causes the insertion or the unplugging of the plug is provided at the socket or is associated with the socket.

An automatic insertion or ejection aid that automatically assists or entirely effects the insertion or unplugging movement is used in the inventive patient bed. The operator is thus largely or completely unburdened of these tasks by this automatic insertion or ejection aid. Because it is an automatic aid, the manual ejection aids described above in the form of the cover lid lever arms are consequently no longer required, or if they are provided as before and their operation is assisted, they can be very significantly unburdened in terms of force since the automatic aid generates the majority of the force to be applied for plug movement and this force no longer is applied by the pivoting cover lid or its lever arms.

Depending on the design of the automatic movement aid, the insertion or unplugging of the plug consequently becomes significantly simpler and more comfortable for the user and damage to the patient bed is safely avoided.

In an embodiment, the automatically operating force generator is a pump that communicates with at least one sealed space fashioned between the socket and the plug and with which a negative pressure assisting or effecting the insertion, or an overpressure effecting the unplugging, can be generated in the space. This inventive embodiment thus utilizes a pneumatic circuit for assisting and effecting the insertion or unplugging movement. A pump is typically already provided at the patient bed, with which a vacuum is generated with which a mat or the like for the patient to lie on can be fixed on the bed. This pump can now be used in order to automatically provide the required force for plugging or unplugging the plug. Here the pump or the negative pressure or overpressure generated thereby represents the force source that is required to assist or implement the plug movement. Depending on the operation of the pump, the plugging or the unplugging can be assisted or affected. If the pump operates in suction mode, thus if the sealed space to be evacuated, a negative pressure is thus generated that leads to the situation of the plug to be inserted being firmly pulled into the socket. If the pump operates in pump operation, an overpressure that pushes the plug out of the socket can be generated in the space. This pneumatic embodiment thus offers the possibility to assist or to effect both plug movements (thus the plugging and the unplugging) depending on the pump operation.

The hollow space with which the pump communicates can be provided in the region of the socket and plug contacts according to a first embodiment. A sealing element acting radially outwardly is typically provided at the socket, this sealing element acting on the plug. This prevents fluid from accumulating in this region by penetrating into the contact region, which can lead to severe damages. This hollow space that already forms upon the insertion is inventively utilized, this hollow space being sealed by the radial sealing element by virtue of it being connected with the pump by a suitable conduit. The hollow space is naturally sufficiently large at the beginning of the plugging movement; with increasing negative pressure, the plug is drawn increasingly further into the socket so that the hollow space decreases in volume until the plug has reached the end position. In the reverse case, air is pumped into the (naturally now small) hollow space by the pump so that the plug is pushed out with continuous enlargement of the hollow space volume.

As an alternative to the formation of the hollow space between the socket and plug contacts, it is also possible to provide it in the region of a socket-side plug guide or to form it upon insertion of the plug. As already described, a number of individual (frequently very thin) contacts are provided on the plug and socket side. In order to enable a secure and damage-free contacting, a plug guide is typically provided. This usually embodies two recesses provided on the socket side, into which recesses corresponding guide pins that protrude at the plug are inserted largely without play. Using the pump it is now possible to evacuate the resulting hollow space after the insertion of the guide pins of the plug that remains in the recess, with the corresponding hollow spaces preferably being used at both recesses or guide pins. The plug can thus be "sucked" into the socket. In reverse, air can be pressed into these hollow spaces to assist unplugging. To seal the hollow spaces it is sufficient to provide corresponding radial sealing elements at the recesses.

It is appropriate to arrange a valve in a conduit leading from the socket to the pump, this valve is closed in the absence of the plug. This means that the pump (which is, for example, in suction mode) does not continuously draw air via the open socket, but instead the conduit is closed via the valve. In order to then immediately open the valve when the automatic plugging assistance is required, a sensor element for detection of the presence of a plug is appropriately provided at the socket, with the valve position being controlled dependent on the detection of a plug. If a plug to be inserted is sensed via an arbitrary sensor element (optical, electrical etc.), the valve is thus immediately opened and the pump can consequently evacuate the hollow space then forming. As long as the plug is detected, the conduit also remains open, meaning that the pump continuously draws air. It is also naturally conceivable to detect the plug reaching the end position via the sealing element in order to then close the valve again.

Depending on the embodiment, the valve remains continuously open as described or is closed after reaching the end position. In the first case, when the unplugging procedure should be assisted or effected an overpressure is established in the hollow space merely by reversing the pump. In the other case it is required to open the valve again beforehand, which can ensue (for example) by an appropriate opening signal being provided to the valve controller via an actuation element in the region of the socket. The actuation element is operated by a user to cause the valve to immediately open, and the pump is reversed.

It is particularly appropriate for a number of sockets to be provided at the bed, which is typically the case since various local coils are to be arranged and contacted at different positions. These multiple sockets are now appropriately connected via separate conduits with a central pump that, as described, is typically already integrated at the bed, with a valve for closing the conduit in the absence of a plug in the associated plug connection being associated with each conduit. It can thereby be ensured that the pump does not continuously draw air via the sockets when the valves are closed due to no detected plug, which could lead to a noise disturbance.

As an alternative or in addition to the pneumatic embodiment of the force generator, the force generator can include at least one spring element that is compressed upon plugging and that assists or effects the unplugging. This inventive alternative is primarily intended as an unplugging aid. At least one spring element (preferably a coil spring) is provided that is compressed in the insertion of the plug and assists the pulling movement when the plug should be drawn out again. The spring element thus serves as a force source or force storage, like the negative pressure or overpressure (the pump) in the previously described embodiment. The spring element is preferably arranged in a bushing-like plug guide in which a guide pin of the plug is accommodated, as described above. During the insertion movement the spring element is compressed. Naturally it is appropriate to arrange a spring element to increase the assisting force in the typically-provided two plug guides (thus the socket-side recesses) so that two force storages are provided. For example, the plugging can be effected or assisted pneumatically while one or two spring elements are simultaneously compressed. If the pump continuously remains on, the plug remains fixed and the spring elements remain compressed. If the pump is deactivated, the plug is ejected or the manual unplugging is assisted via the relaxing spring element or elements. The two mechanical force generators, pneumatic and spring, can also be combined.

In an embodiment of the invention that the spring element can be held in the compressed position by a releasable arresting element. This prevents the plug, when plugged in, from being continuously charged with the return force that would continuously strive to displace the plug at the socket again when the complete unplugging procedure is effected. The releasable arresting element blocks the respective spring element so that this cannot relax. The blocking action occurs when the plug has reached its end position, consequently a complete electrical contact is established. This invention embodiment simultaneously provides information to the user as to whether and when the plug is correctly plugged in. When the plug is not correctly plugged in and the spring elements are thus not arrested, the plug is inevitably pushed out from the socket. The user thus immediately sees whether he or she has correctly effected the contacting, or whether the user must plug the plug in again.

The arresting element can be mechanically or electromechanically operable. A mechanical arresting element can be actuated by the user, for example by a release lever or the like. If it is actuated, the arresting is immediately removed, the force storage can relax and assist or effect the unplugging movement. The use of an electromechanical arresting element that is actuated by a control signal is also conceivable. For example, a switch that is operated by the user can be located in the socket region, upon actuation of a small servomotor or the like unlatches the arresting element. Alternatively, a pneumatically operable arresting element can be provided that, for example, can be actuated by the aforementioned pump that is frequently provided anyway at the bed, for example by this pump drawing the arresting pins or the like out from the arresting position by means of a vacuum after the user has, for example, opened the valve by a corresponding element or the like. Other different embodiments are conceivable for operating the arresting element.

Usually the user does not have to rush to remove the individual plugs from the corresponding sockets when the examination has ended and the patient is moved out from the magnetic resonance apparatus. However, an emergency situation may arise, for example in the case of a quench of the superconducting magnet, in which situation the patient must be brought out from the examination chamber as quickly as possible. However, the patient is more or less immovably "strapped" to the patient bed by the one or more local coils. If the operator must now separately pull each coil plug (and given multiple or large-area local coils it is not unusual to have a considerable number of sockets occupied with plugs), the entire procedure takes a substantial amount of time, which is not acceptable in this situation. In order to counteract this, in an embodiment of the invention a number of sockets at the bed, provided with a respective force-generators having such a force generator associated therewith, are coupled like a network so that given actuation of a central control element all plugged-in plugs can be manipulated in common to effect a common unplugging. This embodiment allows the prompt unplugging of all plugged-in plugs at the point in time of the operation of the central control element, such that all local coils are immediately detached from the patient bed in terms of their electrical contact. The local coils then can be removed quickly from the bed without further measures so that the patient can descend from the patient bed. Only a network-like coupling of the force generators with a central control element is required with, the particular embodiment of this central control element ultimately depending on whether the unplugging operates pneumatically or electromechanically.

Given pneumatic operation, in an embodiment of the invention actuation of the central control element (here, for example, a switch) the operation of the pump in the suction mode generating negative pressure is immediately reversed so that it switches to the pumping mode and generates overpressure in the hollow spaces. The switching state of the valve is either maintained (insofar as it is continuously open when the plug is plugged in) or all valves are immediately opened (preferably excepting those that are associated with sockets that are not occupied in order to avoid a pressure drop from arising). In this case it is also possible, for example, for the pump to pump distinctly stronger than given a "normal" unplugging procedure since this is an emergency situation. A deactivation of the pump is also possible when additional spring elements are provided that then immediately eject the plugs due to the absent suction force.

As an alternative to the pneumatic embodiment, in an electromechanical embodiment all electromechanical arresting, elements communicate with the central control element via conductors so that all can be commonly activated for release of the arresting elements upon actuation of the control element. All servomotors or other components of the arresting elements are thus simultaneously actuated to release.

Given use of pneumatically operating arresting elements, these are appropriately connected via conduits with a central pump (which can likewise be the typically integrated pump), so that upon actuation of the central control element all arresting, elements can be commonly activated (possibly after opening of corresponding valves integrated into the conduits). Depending on how the arresting elements are to be actuated to release, the pump generates a vacuum or an overpressure.

Each invention alternative represents a safely operating emergency system that ensures that in an emergency all electrical contacts are immediately opened by simple actuation of a central control element that is arbitrarily designed depending on the embodiment of the function of the force generator or arresting elements.

BRIEF DESCRIPTION OF THE DRAWINGS

FIG. 3 shows the arrangement of FIG. 2 in the plugged-in state.

FIG. 4 shows a further inventive embodiment of a socket-plug arrangement with pneumatic assistance.

FIG. 5 shows a further inventive embodiment of a socket-plug arrangement with assistance in the form of spring elements.

FIG. 6 shows the arrangement of FIG. 5 in a plugged-in state.

DESCRIPTION OF THE PREFERRED EMBODIMENTS

Figure 1:
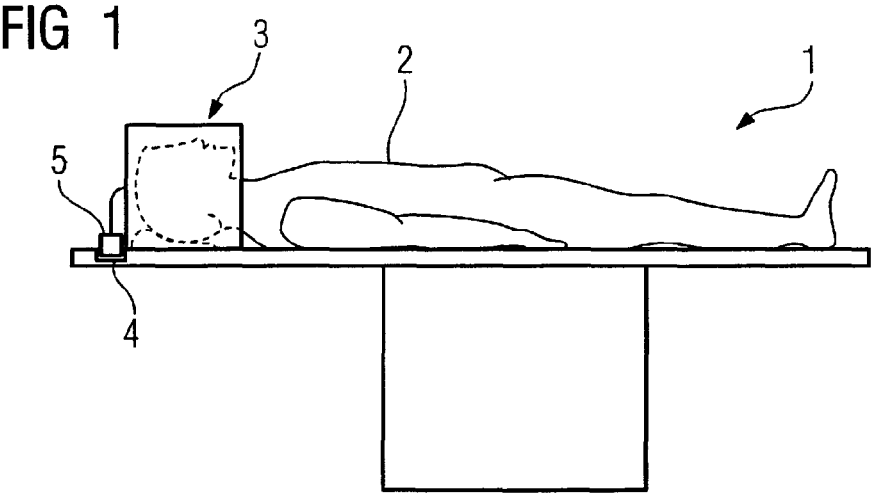
FIG. 1 schematically illustrates an inventive patient bed with local coil attached thereto.

FIG. 1 shows an inventive patient bed 1 on which a patient 2 is arranged. The patient bed 1, which is suitable for a magnetic resonance apparatus, can be displaced vertically in a known manner and the table can be moved horizontally. In the shown example, a local coil 3 (here in the form of a head coil) is arranged at the patient bed 1. For electrical contacting, a socket 4 into which a plug 5 of the local coil 3 is inserted is provided at the patient bed 1. The signal transmission of the image signals acquired by the local coil 3 ensues to a control and processing device (not shown in detail).

Figure 2:
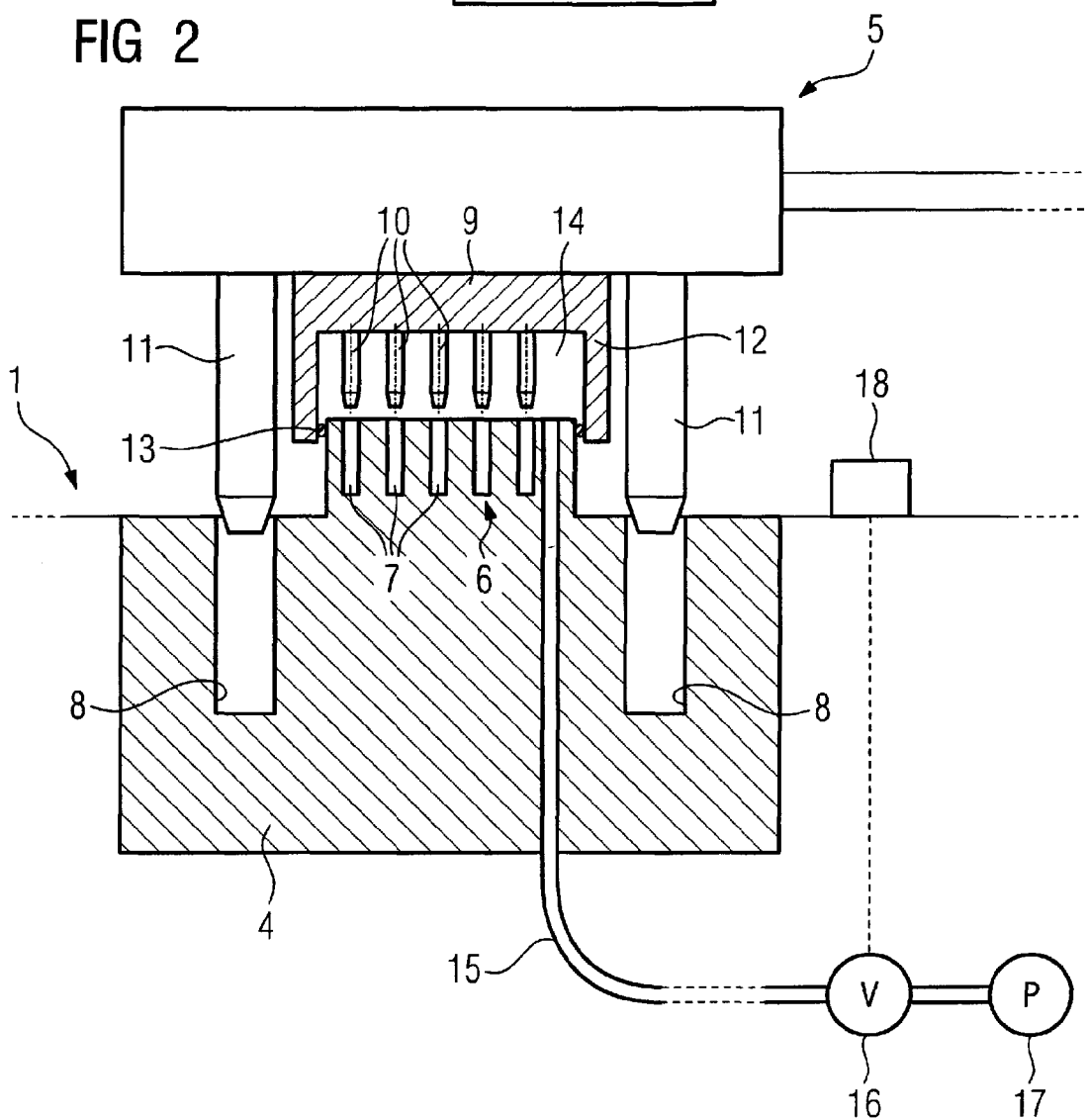
FIG. 2 shows the basic compounds of a socket-plug design of a first embodiment with pneumatic assistance.

FIG. 2 shows a socket-plug arrangement in an enlarged representation. Shown is a section of the patient bed 1 in the region of the socket 4. This has a contact segment 6 with a number of individual socket contacts 7 that are connected with electrical conductors (not shown). Also provided are two plug guides 8 in the form or two recesses.

Also shown is the plug 5 that likewise has a contact segment 9 with a number of individual plug contacts (pins) 10 that, in the plugged-in state, engage in the socket contacts 7. Two projecting guide pins 11 are also provided. As FIG. 2 shows, the guide pins 11 engage in the plug guides 8 in advance of the pins 10 so that an exact guidance of the plug relative to the socket is possible.

The contact segment 9 has a circumferential flange 12 that, as FIG. 2 shows, laterally encompasses the socket contact segment 6. A radially circumferential sealing element 13 is provided at the contact segment 6, which sealing element 13 acts on the inner side of the flange 12 upon insertion of the plug 5. A sealed hollow space 14 thus results. An air conduit 15 in which a valve 16 is connected in the principle representation and that is connected with a pump 17 empties into this hollow space 14 on the socket side. The pump 17 is integrated at the patient bed and, for example, typically serves to apply a vacuum over the bed surface in order to affix possible supports or the like on the bed by vacuum. The valve 16 is optional, thus does not necessarily have to be provided. In this case the air conduit 15 would be continuously open, meaning that air would be continuously drawn via the socket 4 given a continuously running pump 17. Exemplarily provided in FIG. 2 is the valve 17 with which a sensor 18 can be associated if applicable, via which sensor 18 the presence of a plug 5 in the socket 4 is detected. As soon as a plug 5 is detected by the sensor element 18, the formerly closed valve 16 is correspondingly activated and opened so that the air conduit 15 is opened and the pump 17 only then draws air. As described, however, valve 16 and sensor element 18 are optional.

As soon as the hollow space 14 is sealed, the pump 17 generates a negative pressure therein. This negative pressure has the effect that the plug 5 is actively and automatically drawn into the socket 4, consequently the plug contacts 10 are thus inserted into the socket contacts 7. Depending on the magnitude of the generated negative pressure, the plug 5 can be entirely automatically drawn in and therewith contacted, but, it is also possible for the negative pressure to act only in an assistive manner, consequently thus distinctly reducing the force expenditure to be applied by the operator. In FIG. 3 the plug 5 is completely "sucked in", and consequently is in the contact position; the flange 12 lies on the patient bed 1 or on the socket 4. The remaining narrow hollow space 14 can be evacuated further by the pump 17, but it is also possible for the valve 16 (if provided) to be detected by the sensor element 18, then activated so as to be closed after reaching the end position.

If the unplugging movement is to be assisted, it is merely required to reverse the operation of the pump 17 so that the pump 17 generates an overpressure in the small hollow space 14 according to FIG. 3, which overpressure pushes the plug 5 out of the socket 5. For example, for this purpose a separate control element 19 (for example a pushbutton or the like) can be provided in the region of the socket 4, which control element 19 communicates with the pump 17 and via which the pump operation can be reversed. This control element 19 can also communicate with the optionally provided valve so that this is automatically opened when the plug 5 is to be removed. Furthermore, when such a control element 19 is associated with each socket, with a number of sockets being provided at the bed, only the valve 16 that is associated with the socket to be operated is opened as well; all other valves, regardless of whether plugs are plugged therein or not, remain closed in this case.

FIG. 4 shows an alternative embodiment of a socket-plug arrangement. Here as well a partial section of the patient bed 1 with the socket 4 and the plug 5 is shown. However, no air conduit 15 that leads to a hollow space 14 in the region of the socket and plug contacts is provided there, which is different than in the embodiment according to FIG. 2; rather, two air conduits 15 are provided that respectively lead a hollow space 14 that is fashioned in the region of the plug guides 8. The air conduits 15 empty into the plug guides 8. Sealing elements 20 that seal radially towards the guide pins 11 of the plug are respectively provided at the upper end of the plug guides. As soon as the guide pins 11 are thus minimally plugged into the plug guides 8, the corresponding hollow space 14 is fashioned that can then be immediately evacuated via corresponding operation of the pump 14. A negative pressure thus forms via which the plug 5 can be "sucked" toward the socket. Here as well a valve 16 together with associated sensor element 18 can also be optionally provided, just as a control element 19 for pump and valve control can also be optionally provided for realization of an ejection aid.

FIGS. 5 and 6 show a further inventive embodiment of a patient bed 1 and socket-plug arrangement. Shown are the socket 4 and the plug 5, respectively having a socket contact segment 6 with socket contacts 7 and a plug-side contact segment 9 with plug contacts 10. A pure ejection assistance or ejection aid is realized given this invention embodiment. For this a spring element 21 (here in the form of a coil spring) is respectively arranged in each plug guide 8. Upon insertion of the guide pins 11 into the plug guides 8, each spring element 21 is compressed given sustained manual insertion movement (see FIG. 6). The spring elements 21 form a force source or a force storage that is "loaded" by the compression. As soon as the plug 5 has reached its contact end position (see FIG. 6), the plug 5 is arrested in the plugged-in position via an associated arresting elements 22 that can be of an arbitrary nature. The arresting means 22 (here, for example, an arresting pin 23 that can be moved horizontally via a suitable movement mechanism) here engages at one of the guide pins 11 at which a locking recess 24 is provided in the shown example. The entire plug 5 is thereby held in its contact position. The arresting elements 22 can have, for example, a spring element that continuously pre-biases the arresting pin 23 in the direction of the plug guide 8. As soon as the locking recess 24 comes into the locking position shown in FIG. 6, the pin is released and can engage.

If the unplugging of the plug 5 should now be assisted or effected, it is required to release the arresting element 22 again, consequently thus to draw the pin 23 from the catch mechanism in the shown example. This can ensue in different ways. For example, for this it can be drawn back via an electromechanical movement element such as a small servomotor or the like upon actuation of a corresponding control element 25 that activates the actuation element 26. Naturally, in principle it would also be conceivable to effect the pin movement both for engaging and for unlatching exclusively via the actuation element 26. Alternatively, it would also be conceivable to effect the pin movement pneumatically, consequently thus to couple the arresting element 22 by a corresponding conduit with a pump that, for example, moves the pin 23 into the locking position via corresponding pneumatic charging to arrest the pin 23 and draws the pin back again under generation of a negative pressure for releasing. The most different embodiments are conceivable, even a piezoelectric pin or arresting element movement etc.

As soon as the arresting element 22 is released, the two compressed spring elements 21 can relax, which leads to the situation that the plug 5 is pushed out from the socket. Depending on the force that can thereby be generated, the plug can be ejected without manual action of the operator, which requires a sufficient level of force to be provided via the spring elements 21. Alternatively, it is also conceivable that the socket-plug connection is fixed, such that a self-actuating ejection is not possible. The two relaxing force storages (thus the spring elements 21) nevertheless significantly assist the manual unplugging movement.

Figure 7:
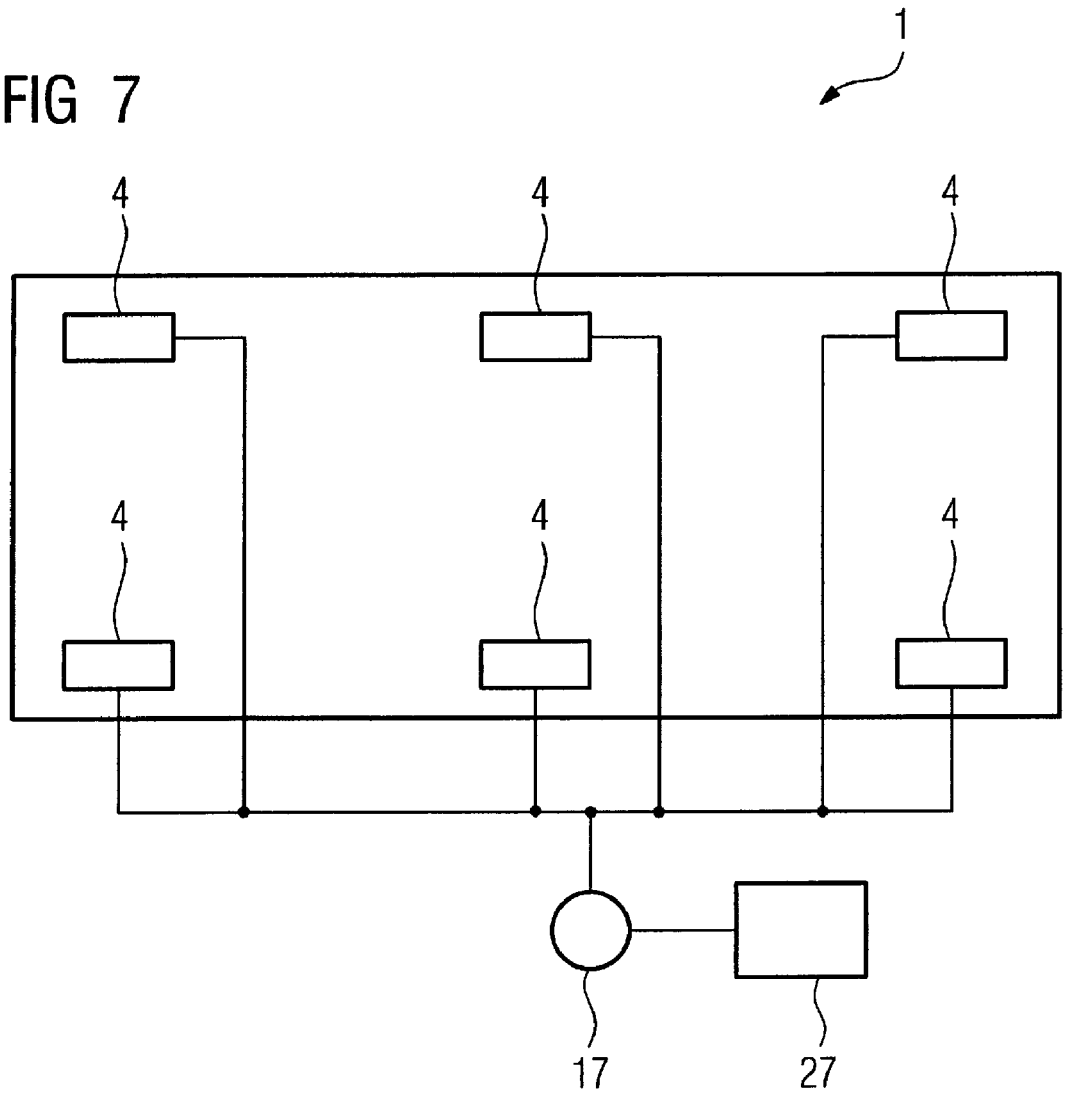
FIG. 7 schematically illustrates a network-like interconnection of the assisting components.

Finally, FIG. 7 shows a principle representation of an inventive patient bed 1 in which a plurality of separate sockets 4 (six in the shown example) are arranged at different positions. They are all connected with a central control element 27 that represents a type of emergency switch and by which it can be effected that all plugs plugged in at the point in time of the switch activation are immediately and jointly ejected. For this the sockets 4 or the arresting element 22 (depending on the embodiment of the respective plug-socket arrangement) are connected with a central actuation element 26 which can, for example, be a pump given a pneumatic embodiment of the plugging or unplugging aid or the arresting element actuation. As soon as the control command is given via the central control element 27 all plugged-in plug connections are to be separated; the operation of the pump 17 is immediately changed to "pump" or the pump 17 is immediately deactivated. This has the effect that, depending on the embodiment, all hollow spaces 14 are set to overpressure and the respective plugs are ejected or all arresting means are, for example, hereby released. As soon as the arresting means are released via a vacuum, the pump operation is naturally set to "suction". In each case all plugs can thus be immediately and automatically released in an emergency so that corresponding local coils can be immediately removed and the patient can leave the bed. Insofar as corresponding valve elements are connected in the conduits, these are naturally likewise correspondingly activated (although it is not shown in detail) so that the ejection operation can take place automatically.

Insofar as the arresting element 22 is electromechanically released, the corresponding actuation elements 26 are naturally to be corresponding activated so that the common release of all arresting element 22 latching at this point in time is possible.

Although modifications and changes may be suggested by those skilled in the art, it is the intention of the inventors to embody within the patent warranted hereon all changes and modifications as reasonably and properly come within the scope of their contribution to the art.

We claim:

1. A patient bed comprising:
   a bed surface configured to receive a patient thereon;
   a socket in said bed surface having electrical socket contacts therein;
   an electrical device configured to interact with the patient while the patient is on the bed surface, said electrical device comprising a plug with electrical plug contacts thereon, said plug being pluggable into, and removable from, said socket to make and break electrical connections between said socket contacts and said plug contacts;
   a force generator associated with said socket that generates a force that interacts with said plug to at least assist at least one plug action selected from the group consisting of insertion of said plug into said socket and removal of said plug from said socket
   said force generator comprising a sealed space between said socket and said plug and a pump communicating with said sealed space, said pump being operable to produce at least one of a negative pressure in said sealed space to pull said plug toward said socket and to generate an overpressure in said sealed space forcing said plug away from said socket; and
   said plug comprising a plug guide and said socket comprising a guide receptacle in which said plug guide moves during said at least one plug action, and wherein said sealed space is formed between said plug guide and said guide receptacle upon insertion of said plug into said socket.

2. A patient bed as claimed in claim 1 wherein said patient support surface is configured for insertion into a magnetic resonance apparatus, and wherein said electrical device is a local coil that radiates or receives radio frequency signals in said magnetic resonance apparatus.

3. A patient bed as claimed in claim 1 wherein said sealed space is formed between said socket contacts and said plug contacts upon insertion of said plug in said socket.

4. A patient bed as claimed in claim 1 comprising a conduit between said socket and said pump, and a valve arranged in said conduit that is closed when said socket does not have said plug therein.

5. A patient bed as claimed in claim 4 comprising a sensor that emits a sensor signal upon detection of said plug at said socket, and wherein said valve is operable between a closed state and an open state dependent on said sensor signal.

6. A patient bed as claimed in claim 1 comprising a plurality of sockets, including said socket, that respectively receive a plurality of different plugs of different electrical devices, and comprising a plurality of conduits respectively connecting a sealed space in each plug and socket combination with said pump, to generate a force at each plug and socket combination to assist or completely defect said at least one plug action.

7. A patient bed as claimed in claim 6 comprising, at each socket in said plurality of sockets, a sensor that emits a sensor signal upon detection of a plug at that socket, and comprising a plurality of valves respectively arranged in said conduits, each valve being controlled by the sensor signal at the socket associated with that conduit, to operate the valve between an open state and a closed state dependent on the sensor signal.

8. A patient bed as claimed in claim 6 wherein said pump is operable to generate a negative pressure in the respective sealed spaces of the respective plug and socket combinations and comprising a manually actuatable control element that, upon activation, reverses operation of said pump to produce an overpressure in the respective sealed spaces to substantially simultaneously force each plug out of each socket.

9. A patient bed as claimed in claim 1 comprising a plurality of sockets, including and corresponding to said socket, at said bed surface that respectively receive a plurality of plugs of a respective plurality of electrical devices, each socket having a force generator associated therewith, and said force generators being coupled to each other in a network comprising a central control element that simultaneously operates said force generators to simultaneously at least assist said at least one plug action for all of said plugs in all of said sockets.

10. A patient bed as claimed in claim 9 wherein said force generators comprise, in each socket, a sealed space formed upon insertion of the plug in that socket, and a single pump communicating with all of said sealed spaces, said pump being operable in a suction mode to produce a negative pressure in each sealed space to pull each plug into each socket, and being operable in a pumping mode to generate an overpressure in each sealed space to force each plug out of said socket, and said force generators comprising, in each socket, a spring element located between the plug and that socket that is compressed upon insertion of the plug in that socket and a pneumatically operable arresting element that holds said spring in a compressed state and that, when actuated, releases said spring from said compressed state to produce a force that pushes the plug out of the socket, and wherein said central control element simultaneously reverses operation of said pump from said suction mode into said pumping mode and actuates all arresting elements to release each spring element from the compressed state.

11. A patient bed as claimed in claim 10 comprising a conduit between each sealed space and said pump, and a valve in each conduit that is closed after complete insertion of the plug in the socket, and wherein said control element, simultaneously with reversing operation of the pump and actuation of the arresting elements, operates each valve to open each valve.

12. A patient bed comprising:
   a bed surface configured to receive a patient thereon;
   a socket in said bed surface having electrical socket contacts therein;
   an electrical device configured to interact with the patient while the patient is on the bed surface, said electrical device comprising a plug with electrical plug contacts thereon, said plug being pluggable into, and removable from, said socket to make and break electrical connections between said socket contacts and said plug contacts;
   a force generator associated with said socket that generates a force that interacts with said plug to at least assist at least one plug action selected from the group consisting of insertion of said plug into said socket and removal of said plug from said socket; and
   said force generator comprising a compressible spring element that is located between said plug and said socket, and that is mechanically compressed upon insertion of said plug in said socket.

13. A patient bed as claimed in claim 12 wherein said plug comprises a plug guide and wherein said socket comprises a guide receptacle in which said plug guide is movable during insertion and removal of said plug relative to said socket, and wherein said spring element is disposed in said plug guide.

14. A patient bed as claimed in claim 12 comprising an actuatable arresting element disposed to interact with said spring element to hold said spring element in a compressed state and, upon actuation of said arresting element, to release said spring element from said compressed state to force said plug out of said socket.

15. A patient bed as claimed in claim 14 wherein said actuatable arresting element is an arresting element selected from the group consisting of mechanically operable arresting elements, electro-mechanically operable arresting elements and pneumatically operable arresting elements.

16. A patient bed as claimed in claim 14 comprising a plurality of sockets, including said socket, that respectively receive plugs in a plurality of plugs respectively of a plurality of electrical devices, each of said sockets and said plurality of sockets comprising an arresting element corresponding to said arresting element, and said patient bed comprising a central control element that is operable to simultaneously actuate all of said arresting elements to simultaneously release each spring element in each socket form the compressed state.

* * * * *